US00PP29555P2

(12) United States Plant Patent
Qiangmin et al.

(10) Patent No.: US PP29,555 P2
(45) Date of Patent: Jul. 31, 2018

(54) ***CAMELLIA* PLANT NAMED 'HA0326'**

(50) Latin Name: *Camellia japonica x Camellia changii*
Varietal Denomination: HA0326

(71) Applicants: Zhao Qiangmin, Guangzhou (CN); Zhao Shanshan, Guangzhou (CN); Wang Jing, Guangzhou (CN)

(72) Inventors: Zhao Qiangmin, Guangzhou (CN); Zhao Shanshan, Guangzhou (CN); Wang Jing, Guangzhou (CN)

(73) Assignee: Palm Eco-Town Development Co. Ltd., Guangzhou (CN)

( * ) Notice: Subject to any disclaimer, the term of this patent is extended or adjusted under 35 U.S.C. 154(b) by 0 days.

(21) Appl. No.: 15/530,360

(22) Filed: Dec. 30, 2016

(51) Int. Cl.
*A01H 5/02* (2018.01)

(52) U.S. Cl.
USPC ..... Plt./243

(58) Field of Classification Search
USPC ..... Plt./243, 244, 245
CPC ..... A01H 5/02; A01H 5/00
See application file for complete search history.

*Primary Examiner* — June Hwu
(74) *Attorney, Agent, or Firm* — C. A. Whealy

(57) ABSTRACT

A new and distinct cultivar of *Camellia* plant named 'HA0326', characterized by its sturdy upright plant habit; rapid growth habit; freely branching habit; dense and bushy appearance; leathery dark green-colored leaves; flowering during the summer, autumn and winter; large light red-colored single-type flowers with white-colored margins; and good garden performance.

2 Drawing Sheets

Botanical designation: *Camellia japonica* x *Camellia changii.*

Cultivar denomination: 'HA0326'.

BACKGROUND OF THE INVENTION

The present Invention relates to a new and distinct cultivar of *Camellia* plant, botanically known as *Camellia japonica* x *Camellia changii*, and hereinafter referred to by the name 'HA0326'.

The new *Camellia* plant is a product of a planned breeding program conducted by the Inventors in Zhaoqing, China. The objective of the breeding program is to create new fast-growing *Camellia* plants that flower year-round and tolerate full sunlight.

The new *Camellia* plant originated from a cross-pollination conducted by the Inventors in October, 2006 in Zhaoqing, China of *Camellia japonica* 'Tama Beauty', not patented, as the female, or seed, parent with an unnamed seedling selection of *Camellia changii*, not patented, as the male, or pollen, parent. The new *Camellia* plant was discovered and selected by the Inventors as a single plant from within the progeny of the stated cross-pollination in a controlled environment in Zhaoqing, China in September, 2011.

Asexual reproduction of the new *Camellia* plant by grafting cuttings onto an unnamed selection of *Camellia gaozhouensis*, not patented, in a controlled greenhouse environment in Zhaoqing, China has shown that the unique features of this new *Camellia* plant are stable and reproduced true to type in successive generations.

SUMMARY OF THE INVENTION

Plants of the new *Camellia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'HA0326'. These characteristics in combination distinguish 'HA0326' as a new and distinct cultivar of *Camellia:*

1. Sturdy upright plant habit.
2. Rapid growth habit.
3. Freely branching habit, dense and bushy appearance.
4. Leathery dark green-colored leaves.
5. Flowering during the summer, autumn and winter.
6. Large light red-colored single-type flowers with white-colored margins.
7. Good garden performance, tolerant to full sunlight conditions.

Plants of the new *Camellia* differ from plants of the female parent, 'Tama Beauty', primarily in the following characteristics:

1. Flowers of plants of the new *Camellia* have fewer stamens than flowers of plants of 'Tama Beauty'.
2. Plants of the new *Camellia* flower multiple times during the year whereas plants of plants of 'Tama Beauty' flower once a year.

Plants of the new *Camellia* differ primarily from plants of the male parent selection in the following characteristics:

1. Leaves of plants of the new *Camellia* are elliptic in shape whereas leaves of plants of the male parent selection are lanceolate in shape.
2. Margins of leaves of plants of the new *Camellia* are serrate whereas margins of leaves of plants of the male parent selection are entire.
3. Plants of the new *Camellia* and the male parent selection differ in flower color as plants of the male parent selection have solid red-colored flowers.

Plants of the new *Camellia* can also be compared to the plants of *Camellia* 'Yu Zhi Pu', not patented. In side-by-side comparisons plants of the new *Camellia* differ from plants of the 'Yu Zhi Pu' in flowering habit as plants of the new *Camellia* flower multiple times during the year whereas plants of plants of 'Yu Zhi Pu' only flower one time each year. In addition, plants of the new *Camellia* have lighter red-colored flowers than plants of 'Yu Zhi Pu'.

BRIEF DESCRIPTION OF THE PHOTOGRAPHS

The accompanying colored photographs illustrate the overall appearance of the new *Camellia* plant showing the colors as true as it is reasonably possible to obtain in colored reproductions of this type. Colors in the photographs may differ slightly from the color values cited in the detailed botanical description, which accurately describe the colors of the new *Camellia* plant.

The photograph on the first sheet is a side perspective view of a typical flowering plant of 'HA0326' grown in a container.

The photograph on the second sheet are close-up view of typical vegetive stems, developing flower buds and developing flowers of 'HA0326'.

DETAILED BOTANICAL DESCRIPTION

The aforementioned photographs and following observations and measurements describe plants grown in Zhaoqing, China in an outdoor nursery during the late autumn and under cultural practices typical of commercial *Camellia* production. During the production of the plants, day temperatures averaged 22° C. and night temperatures averaged 18° C. Plants were five years old when the photographs and description were taken. In the following description, color references are made to The Royal Horticultural Society Colour Chart, 2001 Edition, except where general terms of ordinary dictionary significance are used.

Botanical classification: *Camellia japonica* x *Camellia changii* 'HA0326'.

Parentage:

*Female, or seed, parent.*—*Camellia japonica* 'Tama Beauty', not patented.

*Male, or pollen, parent.*—Unnamed seedling selection of *Camellia changii*, not patented.

Propagation:

*Type.*—By grafting cuttings onto a rootstock, an unnamed selection of *Camellia gaozhouensis*, not patented.

*Time to produce a rooted young plant, summer.*—About two months days at temperatures about 28° C.

*Time to produce a rooted young plant, winter.*—About two months days at temperatures about 8° C.

Plant description:

*Plant form and growth habit.*—Perennial evergreen shrub; sturdy upright plant habit; vigorous growth habit; rapid growth rate.

*Branching habit.*—Freely branching habit; about two to three primary lateral branches each with about four to five secondary branches; dense and bushy appearance.

*Plant height.*—About 165 cm.

*Plant diameter, area of spread.*—About 85 cm.

*Lateral branch description.*—Length, secondary branches: About 20 cm. Diameter: About 1.1 cm. Internode length: About 2.5 cm. Strength: Strong. Aspect: Upright to about 30° to 40° from vertical. Texture and luster: Smooth, glabrous; slightly glossy; woody with development. Color, young stems: Close to 199A; at the internodes, close to 140D. Color, older stems: Close to 199A.

*Leaf description.*—Arrangement: Alternate, single. Length: About 8.9 cm. Width: About 3.2 cm. Shape: Elliptic. Apex: Acuminate. Base: Cuneate. Margin: Serrate. Venation pattern: Pinnate, arcuate. Texture and luster, upper surface: Smooth, glabrous; leathery; moderately glossy. Texture and luster, lower surface: Smooth, glabrous; leathery; matte. Color: Developing leaves, upper surface: Close to 146A. Developing leaves, lower surface: Close to 147B. Fully expanded leaves, upper surface: Close to 147A; venation, close to 144D; color becoming closer to 144D in the autumn. Fully expanded leaves, lower surface: Close to 146B; venation, close to 146B; color does not change with the seasons.

*Petioles.*—Length: About 1.5 cm. Diameter: About 2.5 mm. Texture and luster, upper and lower surfaces: Smooth, glabrous; moderately glossy. Color, upper and lower surfaces: Close to 137A.

Flower description:

*Flower arrangement and appearance.*—Single-type rotate flowers, flowers terminal and axillary; freely flowering habit with usually about 18 flowers and flower buds developing per plant; flowers face upright to outwardly to dropping.

*Natural flowering season.*—Plants of the new *Camellia* flower during the summer, autumn and winter in Zhaoqing, China.

*Postproduction longevity.*—Plants maintain good flower substance for about ten days on the plant; flowers persistent.

*Fragrance.*—None detected.

*Flower diameter.*—Large, about 11.5 cm.

*Flower depth.*—About 6.2 cm.

*Flower buds.*—Length: About 3.2 cm. Diameter: About 1.8 cm. Shape: Ovoid. Texture and luster: Smooth, glabrous; slightly glossy. Color: Close to 138B.

*Petals.*—Quantity and arrangement: About eight imbricate petals arranged in a single whorl. Length: About 5.7 cm. Width: About 4.8 cm. Shape: Broadly obovate. Apex: Obcordate. Base: Cuneate. Margin: Entire; slightly undulate. Texture and luster, upper and lower surfaces: Smooth, glabrous; matte. Color: When opening, upper and lower surfaces: Close to 46C; margins, close to N155C. Fully opened, upper surface: Close to 50A; margins, close to N155B; venation, close to 53B; color does not change with development. Fully opened, lower surface: Close to 50A; margins, close to N155B; venation, close to 50A; color does not change with development.

*Sepals.*—Quantity and arrangement: About six imbricate sepals arranged in a shallow cup-shaped calyx. Length: About 1.6 cm. Width: About 1.9 cm. Shape: Rounded. Apex: Obtuse. Base: Rotund. Margin: Entire. Texture and luster, upper and lower surfaces: Smooth, glabrous; leathery; moderately glossy. Color: When opening, upper surface: Close to 8C. When opening, lower surface: Close to 8B. Fully opened, upper surface: Close to 143C. Fully opened, lower surface: Close to 143D.

*Peduncles*.—Length: About 4 mm. Diameter: About 3 mm. Aspect: About 25° to 35° from stem axis. Strength: Strong. Texture and luster: Smooth, glabrous; matte. Color: Close to 146B.

*Reproductive organs*.—Androecium: Quantity per flower: About 97. Filament length: About 3.7 cm. Filament color: Close to 29B. Anther shape: Oblong. Anther size: About 2.1 mm by 1 mm. Anther color: Close to 9A. Pollen amount: Scarce. Pollen color: Close to 9A. Gynoecium: Quantity of pistils per flower: Tri-parted. Pistil length: About 3.1 cm. Style length: About 3 cm. Style color: Close to 10B. Stigma color: Close to 10A. Ovary color: Close to 10B.

*Fruits and seeds*.—Fruit and seed production have not been observed on plants of the new *Camellia*.

Garden performance: Plants of the new *Camellia* have been observed have good garden performance and to tolerate rain, wind, full sunlight and temperatures ranging from about −10° C. to about 40° C.

Disease & pest resistant: Plants of the new *Camellia* have not been observed to be resistant to pathogens and pests common to *Camellia* plants.

It is claimed:

1. A new and distinct cultivar of *Camellia* plant named 'HA0326' as illustrated and described.

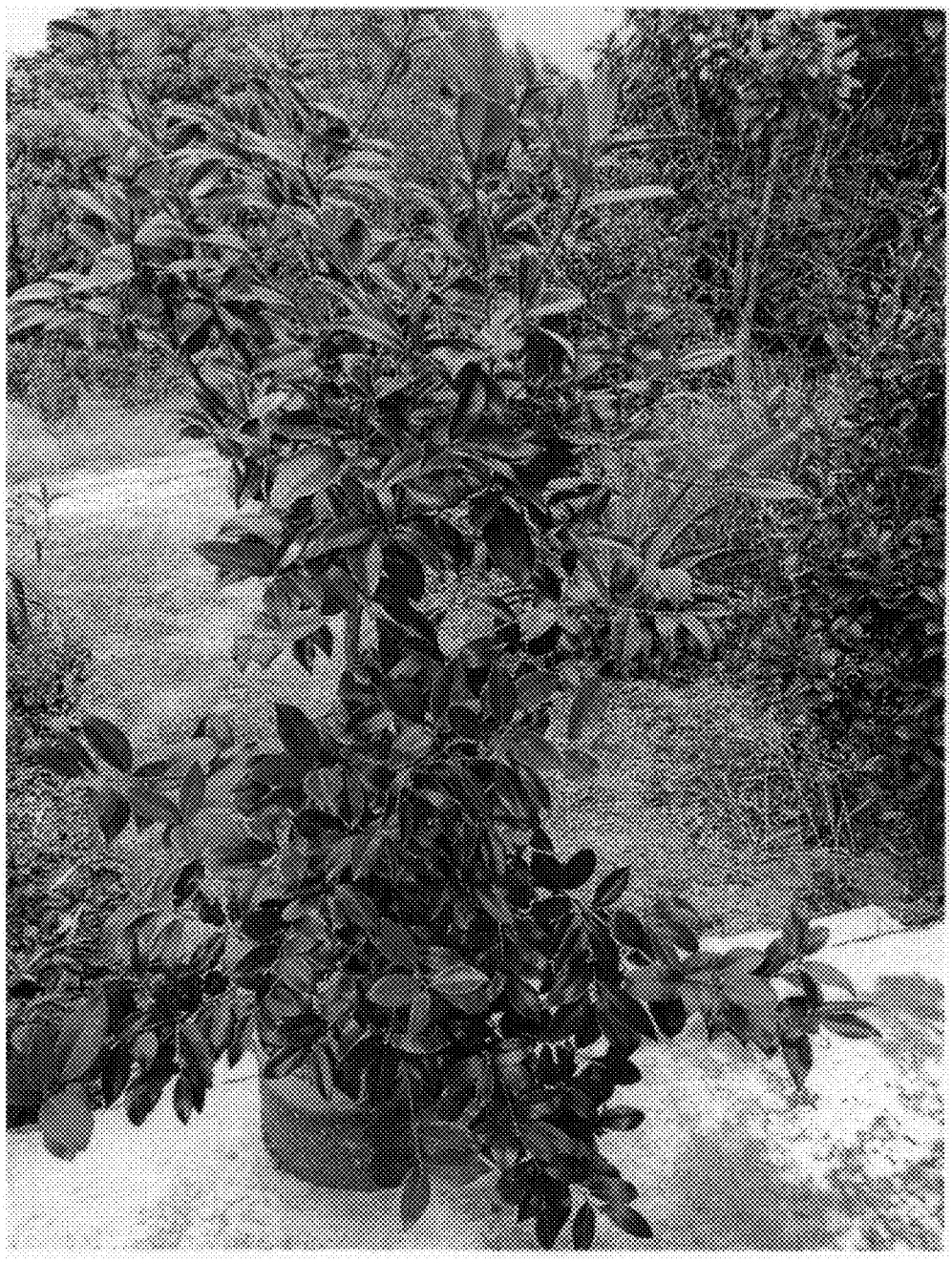

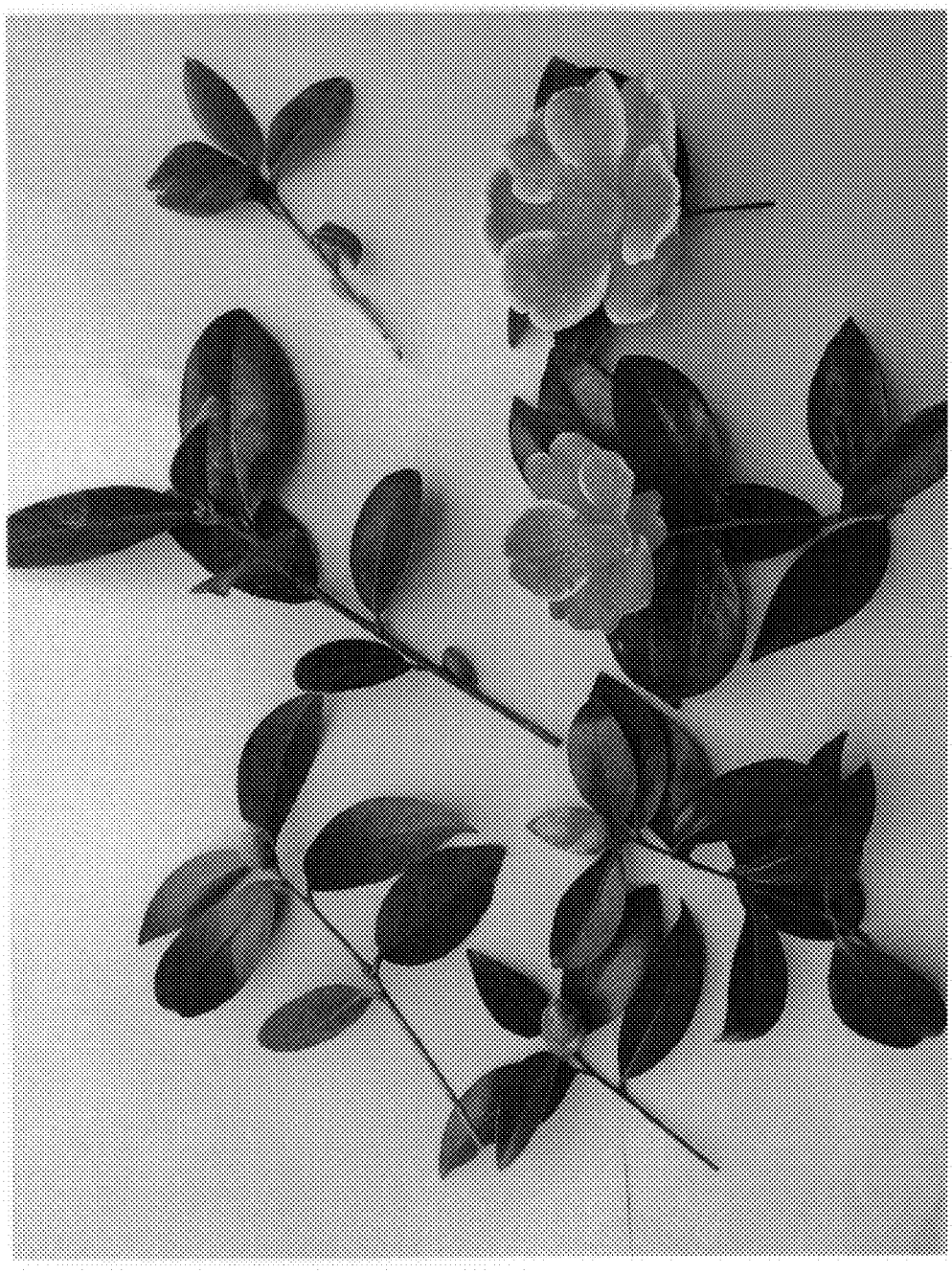

* * * * *